United States Patent [19]

Broger

[11] Patent Number: 5,374,727

[45] Date of Patent: Dec. 20, 1994

[54] ASYMMETRIC HYDROGENATION OF DIHYDRO-PYRIDO [1,2-A]INDOLES

[75] Inventor: Emil A. Broger, Magden, Switzerland

[73] Assignee: Hoffmann-La Roche Inc., Nutley, N.J.

[21] Appl. No.: 68,358

[22] Filed: May 27, 1993

[30] Foreign Application Priority Data

Jun. 19, 1992 [CH] Switzerland .................. 1944/92
Mar. 18, 1993 [CH] Switzerland .................. 826/93

[51] Int. Cl.$^5$ .................. C07D 471/04; C07D 471/02
[52] U.S. Cl. .................................................. 546/95
[58] Field of Search .................................... 546/95

[56] References Cited

U.S. PATENT DOCUMENTS 4,556,740 12/1985 Hansen et al. .................. 568/13

FOREIGN PATENT DOCUMENTS

| 2058112 | 6/1992 | Canada. |
| 3018388 | 5/1980 | Denmark. |
| 39830 | 4/1981 | European Pat. Off. |
| 104375 | 8/1983 | European Pat. Off. |
| 0258967 | 6/1987 | European Pat. Off. |
| 398132 | 5/1992 | European Pat. Off. |
| 492401 | 7/1992 | European Pat. Off. |
| 0492401 | 7/1992 | European Pat. Off. |
| 136605 | of 1978 | Japan. |

OTHER PUBLICATIONS

Chem. Lett. 1985 1007–8.
Abstract (EP 39830), Apr. 29, 1981.
Abstract (EP 398132), May 9, 1992.

Primary Examiner—C. Warren Ivy
Assistant Examiner—D. Margaret M. Mach
Attorney, Agent, or Firm—George M. Gould; George W. Johnston; Robert A. Silverman

[57] ABSTRACT

A process for the asymmetric hydrogenation of 6,7-dihydropyrido[1,2-a]indole-8-methanol or its aromatically-substituted derivatives of the formula

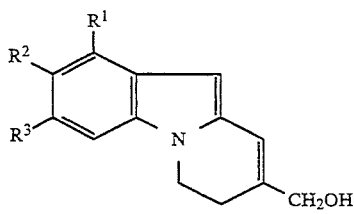

II wherein $R^1$, $R^2$ and $R^3$ each, independently, is hydrogen, halogen, $C_{1-7}$-alkyl, $C_{1-7}$-haloalkyl, hydroxy, $C_{1-7}$-alkoxy, $C_{1-7}$-alkylthio, $C_{1-7}$-alkylsulfinyl, $C_{1-7}$-alkylsulfonyl, nitro, amino or acylamino, to (S)- or (R)-compounds of the formula

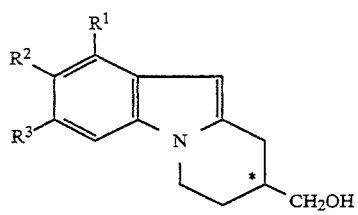

I wherein $R^1$, $R^2$ and $R^3$ have the significances given above and the asterisk (*) denotes the chiral center, carried out using optically active rhodium-diphosphine complexes as catalysts, is described. The production of the compounds II, which also form an object of the invention, is also described. The compounds I and II are valuable intermediates, for example, for the preparation of pharmaceutically active substances.

6 Claims, No Drawings

ASYMMETRIC HYDROGENATION OF DIHYDRO-PYRIDO [1,2-A]INDOLES

BRIEF SUMMARY OF THE INVENTION

The invention relates to a catalytic process for the preparation of compounds of the formula

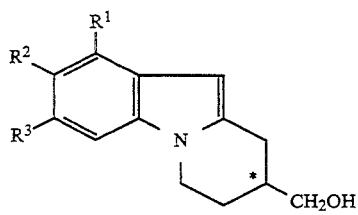

wherein $R^1$, $R^2$ and $R^3$, independently, are hydrogen, halogen, $C_{1-7}$-alkyl, $C_{1-7}$-haloalkyl, hydroxy, $C_{1-7}$-alkoxy, $C_{1-7}$-alkylthio, $C_{1-7}$-alkylsulfinyl, $C_{1-7}$-alkylsulfonyl, nitro, amino or acylamino and the asterisk (*) denotes the chiral center,
in the (S) or (R) form. The compounds of formula I are valuable intermediates, for example, for the preparation of pharmaceutically active substances.

The process in accordance with the invention comprises asymmetrically hydrogenating the corresponding 6,7-dihydropyrido[1,2-a]indole-8-methanol of the formula

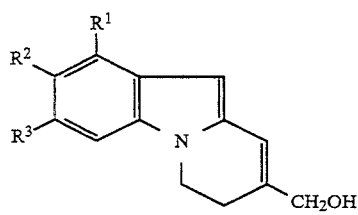

wherein $R^1$, $R^2$ and $R^3$ have the significances given above, in the presence of an optically active rhodium-diphosphine complex.

The starting materials of formula II also form a further object of the invention.

DETAILED DESCRIPTION OF THE INVENTION

The invention relates to a catalytic process for the preparation of compounds of the formula

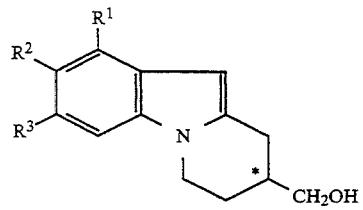

wherein $R^1$, $R^2$ and $R^3$, independently, are hydrogen, halogen, $C_{1-7}$-alkyl, $C_{1-7}$-haloalkyl, hydroxy, $C_{1-7}$-alkoxy, $C_{1-7}$-alkylthio, $C_{1-7}$-alkylsulfinyl, $C_{1-7}$-alkylsulfonyl, nitro, amino or acylamino and the asterisk (*) denotes the chiral center,
in the (S) or (R) form, which comprises asymmetrically hydrogenating the corresponding 6,7-dihydropyrido[1,2-a]indole-8-methanol of the formula

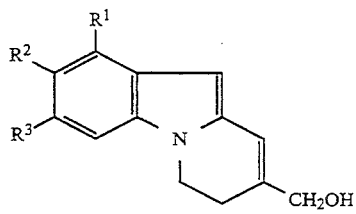

wherein $R^1$, $R^2$ and $R^3$ have the significances given above, in the presence of an optically active rhodium-diphosphine complex.

The starting materials of formula II also form a part of the invention.

As used herein the term "alkyl" denotes alkyl groups which can be straight-chain or branched depending on the number of carbon atoms, which preferably can be 1 to 7 carbon atoms. Exemplary of such groups are methyl, ethyl, propyl, isopropyl, n-butyl, isobutyl, tert-.butyl, n-pentyl, tert.-pentyl, neopentyl, n-hexyl, n-heptyl and the like. The term "haloalkyl", "alkoxy", "alkylthio", alkylsulfinyl" or "alkylsulfonyl" denotes groups wherein the alkyl moiety has the foregoing significance. The term "halogen" denotes fluorine, chlorine, bromine or iodine. The haloalkyl group can have one or more halogen substituents; chloromethyl and trifluoromethyl are examples of such groups. The term "acyl" of the group "acylamino" denotes a group which is derived from an alkanecarboxylic acid of up to 7, preferably up to 4, carbon atoms, such as, for example, formyl, acetyl, propionyl or butyryl, or from an aromatic carboxylic acid, for example, benzoyl.

As rhodium catalysts (optically active rhodium-diphosphine complexes) for the process of the invention, there come into consideration especially those complexes of the formula $$[Rh(X)(Y)(L)_m]_n \qquad \text{III}$$

and $$[Rh(Y)(L)_m]^+ A^- \qquad \text{IV}$$

wherein
X is a coordinating anionic ligand,
Y is an optically active atropisomeric diphosphine ligand,
L is a neutral ligand,
m is 0, 1 or 2,
n is 1 or 2 and
$A^-$ is a non-coordinating anion.

Under the term "a neutral ligand" (L) in the above definition, as applied to formulas III and IV, there is to be understood a readily exchangeable ligand, for example, an olefinic ligand, such as, ethylene, propylene, cycloctene, 1,5-hexadiene, norbornadiene, 1,5-cyclooctadiene and the like, a nitrile, such as, acetonitrile, benzonitrile and the like, or a solvent molecule, for example, of the solvent in which the rhodium catalyst is produced. The neutral ligand can be exchanged in the hydrogenation. Where more than one such ligand is present, that is, m=2, these can also be different from one another. As coordinating anionic ligands (X) and optically active atropisomeric diphosphine ligands (Y), there come into consideration especially the ligands given in the following definition of formulas III' and IV'. The anion A⁻ is also specified in more detail hereinafter.

The catalyst which us used in the process of the invention, preferably, is an optically active rhodium-diphosphine complex of the formula

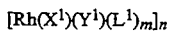  III' or

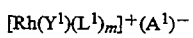  IV' wherein

X¹ is a halide, an anion of the formula R⁴—COO—, an anion of the formula R⁴—SO₃—, 1,3-diketonate or phenolate optionally mono- or multiply-substituted with lower alkyl and/or halogen, Y¹ is an optically active atropisomeric diphosphine ligand of the formula

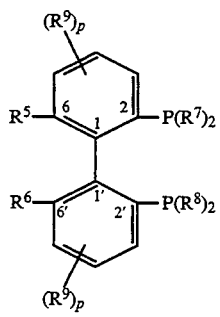  V or of the formula

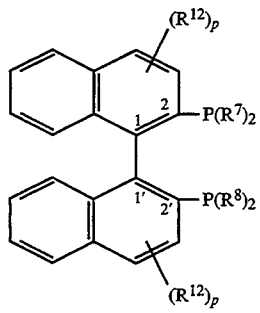  VI

L¹, or each L¹, independently, is an olefinic ligand, a nitrile or a solvent molecule, (A¹)⁻ is BF₄⁻, ClO₄⁻ or PF₆⁻, m is 0, 1 or 2, n is 1 or 2, R⁴ is lower alkyl, halogenated lower alkyl or aryl, R⁵ and R⁶, independently, are lower alkyl, lower alkoxy, di(lower alkyl)amino, hydroxy, protected hydroxy, hydroxymethyl or protected hydroxymethyl or R⁵ and R⁶, taken together, are a divalent group of the formula

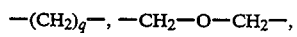

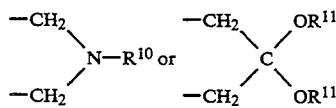

R⁷ and R⁸, independently, are lower alkyl, C₃₋₇-cycloalkyl, optionally substituted phenyl, a five-membered heteroaromatic or a group of the formula

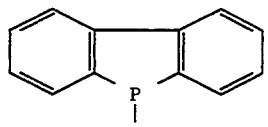

R⁹ is lower alkyl or lower alkoxy,

R¹⁰ is lower alkyl, optionally substituted phenyl or optionally substituted benzyl, R¹¹ is lower alkyl or both R¹¹'s, taken together, are di- or trimethylene, R¹² is halogen, hydroxy, methyl, ethyl, amino, acetamido, nitro or sulfo, p is zero or the number 1, 2 or 3 and q is the number 3, 4 or 5.

In the scope of the above definitions, as applied to formulas III–VI including III' and IV', and in the following explanations, the term "halide" or "halogen" denotes fluorine, chlorine, bromine or iodine. The term "lower alkyl" denotes straight-chain or branched alkyl groups of 1 to 4 carbon atoms, for example, methyl, ethyl, propyl, isopropyl, n-butyl, isobutyl and tert.butyl. The term "lower alkoxy" denotes groups in which the alkyl residue has the foregoing significance. This also applies to other groups containing "lower alkyl", such as, halogenated lower alkyl and di(lower alkyl)amino. As to the "halogenated lower alkyl" groups, there are to be understood lower alkyl groups which are mono- or multi-substituted with the same or different halogen atoms, especially with fluorine and/or chlorine. Preferably, a halogen atom is in the α-position (on residue R⁴) to the —COO⁻. Preferred halogenated lower alkyl groups comprise perchlorinated and perfluorinated lower alkyl groups, such as, trichloromethyl and, respectively, pentafluoroethyl, The term "aryl" denotes, especially, phenyl, biphenyl or naphthyl which is unsubstituted or mono-or multi-substituted with the same or different lower alkyl groups and/or halogen atoms. Preferred halogenated aryl groups for R⁴ are per-chlorophenyl and perfluorophenyl. When the residue R⁷, R⁸ or R¹⁰ is optionally substituted phenyl or, with respect to R¹⁰ alone, optionally substituted benzyl, there come into consideration as substituents, in the case of benzyl for its phenyl moiety, especially fluorine; lower alkyl or alkoxy groups, preferably methyl or methoxy; di(lower alkyl)amino, preferably dimethylamino; tri(-lower alkyl)silyl, preferably trimethylsilyl; and phenyl. As protecting groups for the hydroxy or hydroxymethyl group, R⁵ and/or R⁶ as protected hydroxy or protected hydroxymethyl, there come into consideration, especially, the usual ether-forming groups, such as, benzyl, allyl, benzyloxymethyl, lower alkoxymethyl or also 2-methoxy-ethoxymethyl and the like. The term "five-membered heteroaromatic" in R⁷, R⁸, denotes a substituent of the formula

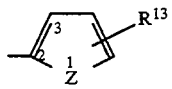  (a)

-continued (b)
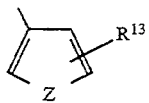

(c)
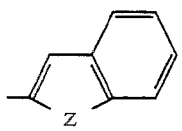

(d)
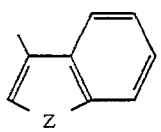

wherein Z is oxygen, sulfur or $NR^{14}$; $R^{13}$ is hydrogen, lower alkyl, especially methyl, or lower alkoxy, especially methoxy, and $R^{14}$ is lower alkyl, especially methyl.

When p, in formula VI, is 1, 2 or 3, both or two of the residues $R^{12}$ are preferably situated in the 5,5'-position.

Under the term "1,3-diketonate", $X^1$ in formula III', there are to be understood especially residues which are derived from aliphatic and aromatic diketones of the formula $R^{15}$—CO—$CH_2$—CO—$R^{15}$, wherein $R^{15}$ is lower alkyl or aryl.

In formulas III and III' X and, respectively, $X^1$ is preferably, halide, especially, the bromide ion.

Preferred ligands Y and $Y^1$ are those of formula V. Of these there are, furthermore, preferred those in which $R^5$ and $R^6$ are the same and each is lower alkyl or lower alkoxy or, alternatively, $R^5$ and $R^6$ taken together are the group —$CH_2$—O—$CH_2$—, and $R^7$ and $R^8$ are the same and each is phenyl which is unsubstituted or mono-or multi-substituted in the 3-, 4- and/or 5-position and $R^9$ is methyl or methoxy and p is 0 or 1. When p in formula V is the number 1, each substituent $R^9$ is preferably situated in the para-position to the respective phosphorus atom.

A complex of formula III or III' is preferably used as the rhodium catalyst for the process in accordance with the invention.

The asymmetric hydrogenation, in accordance with the invention, of a compound of formula II to the corresponding compound of formula I can be effected in a suitable organic solvent which is inert under the reaction conditions. As such solvents, there especially come into consideration, for example, aliphatic esters, such as, ethyl acetate; cyclic ethers, such as, tetrahydrofuran and dioxane; and aromatic hydrocarbons, such as, benzene and toluene; and also mixtures of the above solvents. The hydrogenation is conveniently carried out at temperatures in the range of between about 20° C. and about 140° C., preferably in the temperature range of from about 60° C. to about 120° C., and at a pressure in the range of from about 1 to about 100 bar, preferably of about 2 to about 60 bar. The molar ratio of rhodium to diphosphine ligand Y or $Y^1$ in the complex of formula III or IV, or III' or IV', conveniently is in the range of between about 0.05:1 and about 5:1, preferably between about 0.5:1 and about 2:1. With respect to the molar ratio of rhodium to the coordinating anionic ligand X or $X^1$ in the complex of formula III or III', it conveniently is in the range of between about 0.01:1 and about 20:1, preferably between about 0.5:1 and about 10:1. The percentage molar ratio of rhodium in the rhodium catalyst to the compound of formula II to be hydrogenated, the 37 substrate", conveniently is in the range of between about 0.001 and about 5, corresponding to a molar ratio substrate:catalyst (S/C) of about 100,000 to about 20, preferably between about 0.002 and about 0.2, S/C about 50,000 to about 500.

When a compound of formula I in the (S)-form is to be prepared, then the catalyst used is an optically active rhodiumdiphosphine complex, for example, of formula III or IV, especially of formula III' or IV', in which the optically active atropisomeric diphosphine ligand, for example, is present in the (R)-form. The corresponding diphosphine ligand in the (S)-form is used for the preparation of a (R)-compound of formula I.

The process in accordance with the invention enables the compounds of formula I to be prepared in high optical purity. It is especially preferred for the preparation of (S)-6,7,8,9-tetrahydropyrido[1,2-a]indole-8-methanol, (S)-compound of formula I in which $R^1$, $R^2$ and $R^3$, each, is hydrogen. This compound is a valuable intermediate in the synthesis of (S)-3-{6,7,8,9-tetrahydro-8-[(dimethylamino)methyl]pyrido[1,2-a]indol-10-yl}-4-(1-methyl-3-indolyl)-1H-pyrrole-2,5-dione hydrochloride, a valuable pharmaceutically active substance for the treatment or prophylaxis of diseases, especially, inflammatory, immunological, oncological, bronchopulmonary and cardiovascular diseases.

The optically active rhodium-diphosphine complexes, for example, those of formulas III and III', are either known or can be produced in a known manner, for example, by reacting an optically active atropisomeric diphosphine ligand of formula V or VI with a compound which can yield rhodium in a suitable inert organic or aqueous solvent. As suitable compounds which yield rhodium there can be mentioned, for example, organic rhodium complexes with ethylene, propylene and the like and with dienes, for example, (Z,Z)-1,5-cyclooctadiene, 1,5-hexadiene and bicyclo[2.2.1-]hepta-2,5-diene, which form readily soluble complexes with rhodium. Preferred compounds which yield rhodium are, for example, di-$\mu$-chloro-bis[$\eta^4$-(Z,Z)-1,5-cyclooctadiene]-dirhodium(I), di-$\mu$-chloro-bis[$\eta^4$-norbornadiene]dirhodium(I), di-$\mu$-trifluoroacetato-bis[$\eta^4$-(Z,Z)-1,5-cyclooctadiene]dirhodium(I), bis[$\eta^4$-(Z,Z)-1,5-cyclooctadiene]rhodium tetrafluoroborate and bis [$\eta^4$-(Z,Z)-cyclooctadiene]rhodium perchlorate, The ligands of formulas V and VI are themselves known, for example, from European Patent Publications 104,375 and 398,132 or from Japanese Patent Publication (Kokai) 136,605/1978, or can be obtained in analogy to the production of the known ligands. These publications contain methods for the production of those ligands of formulas V and VI in which $R^7$ and $R^8$ are the same. Those compounds, in which $R^7$ and $R^8$ are different from each other, can be obtained in analogy thereto, although in two steps, for example in accordance with the following Reaction Scheme:

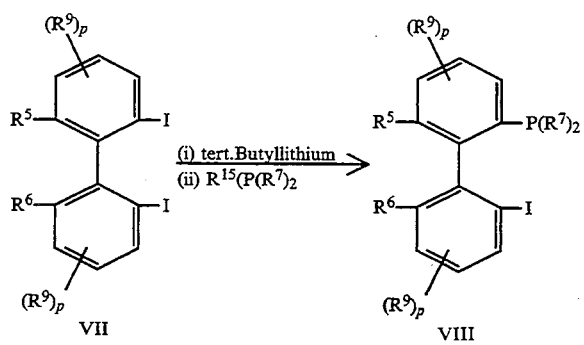

rhodium catalyst can be produced in situ, optionally in the presence or in the absence of the compound to be hydrogenated.

The 6,7-dihydropyrido[1,2-a]indole-8-methanols of formula II which are used as starting materials in the process in accordance with the invention also form an object of the invention. The compounds of formula II can be produced, for example, according to the following Reaction Scheme:

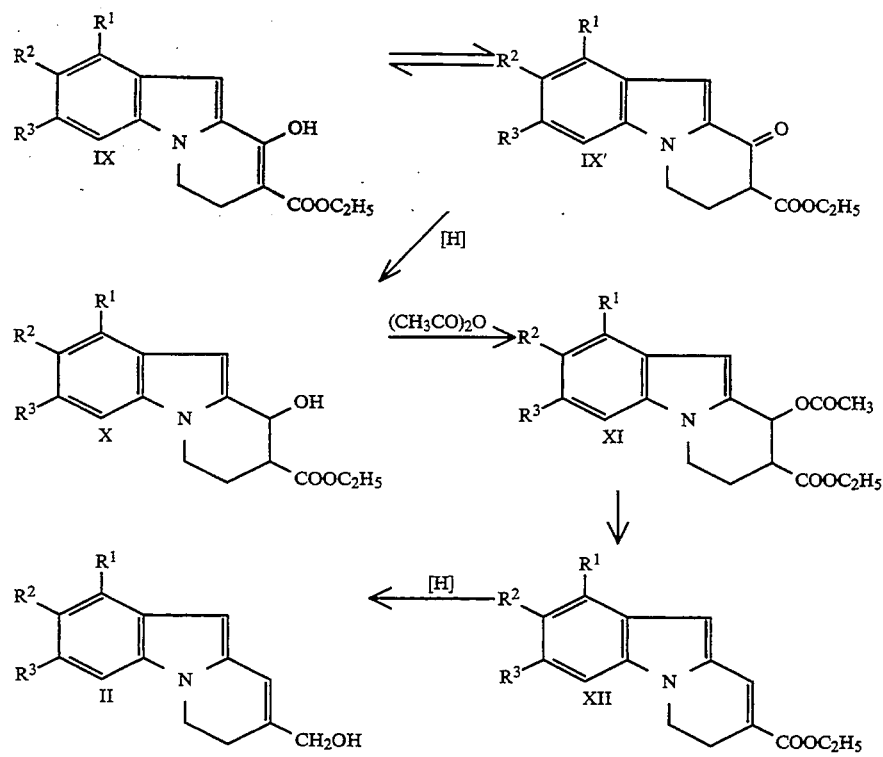

, wherein $R^5$, $R^6$, $R^7$, $R^8$, $R^9$ and p have the significances given above and $R^{15}$ is a leaving group, for example, halogen, especially chlorine or bromine; or alkoxy, especially methoxy or ethoxy. In order to guarantee that only one iodine atom is replaced by a lithium atom using the alkyllithium, for example, tert.butyllithium, the corresponding reactions are conveniently carried out using about equivalent amounts of reaction partners.

In carrying out the asymmetric hydrogenation in accordance with the invention the optically active rhodium-diphosphine complex, for example, that of formula III, III', IV or IV', can firstly be produced and then a solution of the compound of formula II to be hydrogenated is added. Alternatively, however, the The conversion of the optionally substituted ethyl 6,7-dihydro-9-hydroxypyrido[1,2-a]indole-8-carboxylate of formula IX or of the corresponding β-ketoester of formula IX' into the corresponding 6,7,8,9-tetrahydro compound of formula X is conveniently effected using ammonium formate as the reducing agent in the presence of palladium-on-charcoal as the catalyst. Moreover, the reduction is conveniently carried out in an organic solvent, especially ethanol, and at the reflux temperature of the respective reaction mixture. In order to exclude oxygen, as much as possible, from the reductive reaction system, the reaction is conveniently effected under an atmosphere of inert gas, preferably nitrogen.

The next reaction step is an acetylation, which is conveniently carried out using acetic anhydride or acetyl chloride. An organic solvent, for example, an aliphatic ester, such as, ethyl acetate, and a base which is usual for acetylations are conveniently used, although it is more suitable to use an organic solvent which simultaneously serves as the base, for example, pyridine or a substituted derivative thereof, such as, a lutidine or a collidine. The acetylation of the optionally substituted ethyl 6,7,8,9-tetrahydro-9-hydroxypyrido[1,2-a]indole-8-carboxylate of formula X is conveniently effected at temperatures in the range of between about 40° C. and about 90° C.

The resulting ethyl 9-acetoxy-6,7,8,9-tetrahydropyrido-[1,2-a]indole-8-carboxylate formula XI is then subjected to an elimination reaction using a strong base, for example, 1,1,3,3-tetra-methylguanidine or diazabicycloundecane, to give the corresponding ethyl 6,7-dihydropyrido[1,2-a]indole-8-carboxylate of formula XII. This elimination step is conveniently effected in an organic solvent for example, an aromatic hydrocarbon, such as, benzene or toluene, or an aliphatic alcohol, for example, ethanol, and at temperatures in the range of between about 40° C. and about 90° C., depending on the base which is used.

The reduction of the ethyl 6,7-dihydropyrido[1,2-a]indole-8-carboxylate of formula XII, produced in the foregoing reaction step, to the corresponding 8-methanol compound, that is, to the starting material of formula II required for the process in accordance with the invention, is effected using a (mixed) reducing agent which contains lithium ions and borohydride ions, for example, lithium chloride and sodium borohydride, lithium bromide and potassium borohydride. Alternatively, a reducing agent of the lithium borohydride type or diisobutylaluminum hydride type can be used for this purpose. Moreover, the reaction is carried out in a suitable solvent, for example, an aliphatic or cyclic ether, for example, diglyme or tetrahydrofuran or dioxane. In the case of most of the reducing agents which come into consideration, the reaction is carried out at temperatures at about room temperature, but when lithium borohydrides are used the reaction is preferably carried out at the reflux temperature of the reaction mixture.

The Examples which follow further illustrate the invention. The abbreviations used in these Examples have the following meanings:

| TLC | thin-layer chromatography |
| --- | --- |
| GC | capillary gas chromatography |
| e.e. | enantiomeric excess. The e.e. of the hydrogenation product is determined by GC analysis of the diastereomeric ester prepared from camphanoyl chloride (Fluka). |
| BIPHEMP | (6,6'-dimethylbiphenyl-2,2'-diyl)bis(diphenylphosphine) |
| MeOBIPHEP | (6,6'-dimethoxybiphenyl-2,2'-diyl)bis(diphenylphosphine) |

EXAMPLE 1

Preparation of
(R)-6,7,8,9-tetrahydropyrido[1,2-a]indole-8-methanol a) 12.25 mg (0.025 mmol) of di-μ-chloro-bis-(1,5-cyclooctadiene)dirhodium(I) and 29.25 mg (0.050 mmol) of (S)—MeOBIPHEP are suspended in 50 ml of toluene in a 50 ml glass flask in a glove box (oxygen content <1 ppm). The suspension is subsequently stirred for 10 minutes, whereby a clear yellow solution (the catalyst solution) forms.

b) The glass attachment of a 30 ml autoclave is charged in a glove box (oxygen content <1 ppm) with 0.20 g (1.0 mmol) of 6,7-dihydropyrido[1,2-a]indole-8-methanol, 8 ml of toluene and 2 ml of the above-mentioned catalyst solution. The hydrogenation is carried out at 80° C., an initial pressure of 60 bar of $H_2$ and while stirring vigorously. After a hydrogenation time of 18 hours, the conversion is 99.9% according to GC. The pale yellow hydrogenation solution is evaporated. The residue is dissolved in diethyl ether and the solution is allowed to flow through a 5 g silica gel column in order to separate the catalyst. Rinsing of the column with diethyl ether, evaporation of the eluate and drying of the pale brown crystalline residue, yields 0.20 g (100%) of (R)-6,7,8,9-tetrahydropyrido[1,2-a]indole-8-methanol; GC 100 area %, 93.7% e.e.

EXAMPLE 2

Preparation of
(S)-6,7,8,9-tetrahydro[1,2-a]indole-8-methanol a) 9.2 mg (0.0226 mmol) of bis-(1,5-cyclooctadiene)rhodium(I) tetrafluoroborate, 12.4 mg (0.0226 mmol) of (R)-BIPHEMP and 14.6 mg (0.045 mmol) of tetrabutylammonium bromide are suspended in 20 ml of toluene in a 50 ml glass flask in a glove box (oxygen content <1 ppm). The suspension is subsequently stirred for 60 minutes, whereby a clear orange solution (the catalyst solution) forms.

b) A 400 ml autoclave (Hastelloy C4) is charged in a glove box (oxygen content <1 ppm) with 22.5 g (0.113 mol) of 6,7-dihydropyrido[1,2-a]indole-8-methanol, the aforementioned catalyst solution and 130 ml of toluene. The hydrogenation is carried out at 80° C., a constant pressure of 60 bar of $H_2$ and while stirring vigorously. After a hydrogenation time of 16 hours, the conversion is 100% according to GC. Then, 250 ml of diethyl ether are added to the reaction mixture (brown crystal slurry) and the resulting suspension is stirred at 50° C. until all has dissolved. For the crystallization of the product, the solution is evaporated to a weight of 95 g in a partial vacuum and the resulting suspension is stirred at room temperature for 3 hours. The beige crystals are removed by filtration, washed with cold toluene and dried for 18 hours at 40° C./20 mbar. Yield: 19.8 g (87.1%) of (S)-6,7,8,9-tetrahydropyrido[1,2-a]indole-8-methanol; m.p. 107.5°–109.0° C.; TLC 1 spot; GC 100 area %; 98.9% e.e.; $[\alpha]_D^{20}$ −47.2° (c=1, $CHCl_3$).

The mother liquor is filtered through a layer of 5 g of silica gel. Rinsing with 100 ml of diethyl ether and evaporation of the combined filtrate yields an additional 2.44 g (10.7%) of product; GC 100 area %; 97.7% e.e.

EXAMPLE 3

Preparation of
(S)-6,7,8,9-tetrahydropyrido[1,2-a]indole-8-methanol a) 12.3 mg (0.025 mmol) of di-μ-chloro-bis-(1,5-cyclooctadiene)dirhodium(I) and 27.5 mg (0.050 mmol) of (R)-BIPHEMP are suspended in 100 ml of tetrahydrofuran, in a 100 ml measuring flask in a glove box (oxygen content <1 ppm). The suspension is subsequently stirred for 10 minutes, whereby a clear yellow solution (the catalyst solution) forms.

b) The glass attachment of a 30 ml autoclave is charged in a glove box (oxygen content <1 ppm) with 0.20 g (1.0 mmol) of 6,7-dihydropyrido[1,2-a]indole-8-methanol, 9 ml of tetrahydrofuran and 1 ml of the above-mentioned catalyst solution. The hydrogenation is carried out at 80° C., an initial pressure of 60 bar of $H_2$ and while stirring vigorously. After a hydrogenation time of 18 hours, the conversion is 99.9% according to GC. The pale yellow hydrogenation solution is evaporated. The residue is dissolved in diethyl ether and, in order to separate the catalyst, the solution is allowed to flow through a 5 g silica gel column. Rinsing of the column with diethyl ether, evaporation of the eluate and drying of the pale brown crystalline residue yields 0.20 g (100%) (S)-6,7,8,9-tetrahydropyrido[1,2-a]indole-8-methanol; GC 100 area %; 91.0% e.e.

EXAMPLES 4–10

Preparation of (R)- or (S)-6,7,8,9-tetrahydro[1,2-a]indole-8-methanol

Hydrogenations are carried out using a rhodium catalyst of formula III' ([Rh(X$^1$)(Y$^1$)(L$^1$)$_m$[$_n$]) analogously to the procedure described in Example 1, 2 or 3 in order to convert 6,7-dihydropyrido[1,2-a]indole-8-methanol into (R)- and (S)-6,7,8,9-tetrahydro[1,2-a]indole-8-methanol. As in Examples 1–3, each hydrogenation is carried out in toluene at 80° C. and a constant pressure of 60 bar of H$_2$. The substrate:catalyst molar ratio is 2000 in each case. The respective catalyst, conversion after 18 hours according to GC, the enantiomeric excess (e.e.) and the configuration [(R)/(S)] of the ligand Y$^1$ and of the product, are given in the following Table.

TABLE

| | | Catalyst used Rh(X$^1$)(Y$^1$)(COD) | | | | | | | Config. of the product |
|---|---|---|---|---|---|---|---|---|---|
| | | | Y$^1$ (p = zero in each case) | | | | Conversion | | |
| Example | X$^1$ | Formula | R$^5$=R$^6$ | R$^7$ | R$^8$ | Config. | sion | e.e. % | (R)/(S) |
| 4 | Cl | V | CH$_3$ | Phenyl | 2-Thienyl | (R) | 100 | 94.0 | (S) |
| 5 | Cl | V | CH$_3$ | Phenyl | Cyclopentyl | (R) | 100 | 82.1 | (S) |
| | | | | R$^7$=R$^8$ | | | | | |
| 6 | Cl | V | OCH$_3$ | 3,5-Dimethyl-4-dimethylamino-phenyl | | (S) | 99 | 96.4 | (R) |
| 7 | Cl | V | OCH$_3$ | 3,5-Diphenyl-phenyl | | (S) | 100 | 90.1 | (R) |
| 8 | Cl | V | OCH$_3$ | 2-Furyl | | (R) | 99 | 84.4 | (S) |
| 9 | Br | VI | — | p-Tolyl | | (R) | 100 | 94.5 | (S) |
| 10 | CH$_3$COO | V | CH$_3$ | Phenyl | | (R) | 91 | 79.7 | (S) |

EXAMPLE 11

Preparation of 6,7-dihydropyrido[1,2-a]indole-8-methanol

A mixture of 18 g (0.07 mmol) of ethyl 6,7-dihydro-9-hydroxypyrido[1,2-a]indole-8-carboxylate and 13.3 g of 0.21 mmol) of ammonium formate in 300 ml of ethanol is treated under a nitrogen atmosphere with 2.2 g of 10% palladium/charcoal and heated to reflux temperature for 4 hours. The resulting suspension is cooled to room temperature, filtered and the solid is washed with 50 ml of ethanol and twice with 50 ml of methylene chloride, each time. Then, the filtrate and the washings are evaporated and the residue is taken up in a mixture of ethyl acetate and water (5:4, total 450 ml). The organic phase is washed with 100 ml of sodium chloride solution, dried over anhydrous sodium sulfate and evaporated to dryness. In this manner, there are obtained 17.5 g (96%) of ethyl 6,7,8,9-tetrahydro-9-hydroxypyrido[1,2-a]indole-8-carboxylate as a beige solid, m.p. 116°–120° C.

A solution of 75 g (0.29 mmol) of ethyl 6,7,8,9-tetrahydro-9-hydroxypyrido[1,2-a]indole-8-carboxylate in 1000 ml of pyridine is treated dropwise within 10 minutes with 59.2 g (0.58 mol) of acetic anhydride. The reaction mixture is heated at 50° C. for 24 hours and the solvent is subsequently evaporated. The residue is taken up in a mixture of ethyl acetate and water (2:1, total 750 ml) and the organic phase is washed with 250 ml of water and twice with 100 ml of 1N hydrochloric acid each time, dried over anhydrous sodium sulfate and evaporated to dryness. In this manner, there are obtained 87 g (100%) of ethyl 9-acetoxy-6,7,8,9-tetrahydropyrido[1,2-a]indole-8-carboxylate as a pale yellow solid, m.p. 98°–100° C.

A solution of 9.93 g (0.033 mol) of ethyl 9-acetoxy-6,7,8,9-tetrahydropyrido[1,2-a]indole-8-carboxylate in 150 ml of toluene is treated with 8.3 ml (0.066 mol) of 1,1,3,3-tetra-methylguanidine and the reaction mixture is heated at 80° C. for 17 hours. The resulting solution is then cooled to room temperature, washed in succession three times with 50 ml of 1N hydrochloric acid each time, 50 ml of aqueous sodium bicarbonate solution and 50 ml of sodium chloride solution, dried over anhydrous sodium sulfate and evaporated to dryness. After trituration of the residue with n-hexane, there are obtained 6.64 g (83%) of ethyl 6,7-dihydropyrido[1,2-a]indole-8-carboxylate as a pale yellow solid, m.p. 77°–79° C.

A solution of 26 g (0.108 mol) of ethyl 6,7-dihydropyrido[1,2-a]indole-8-carboxylate in 850 ml of dry tetrahydrofuran is treated dropwise within 1 hour under a nitrogen atmosphere with a 1M solution of diisobutylaluminium hydride in tetrahydrofuran (220 ml, 0.22 mol). The reaction mixture is stirred for 17 hours and 50 ml of methanol are subsequently added dropwise. After the addition of 1000 ml of water and 500 ml of toluene, the mixture is filtered and the aqueous part of the filtrate is separated and extracted with 250 ml of toluene. The combined organic phases are then dried over anhydrous sodium sulfate and evaporated to dryness. There are obtained 19.8 g (92%) of 6,7-dihydropyrido[1,2-a]indole-8-methanol as a beige solid, m.p. 139°–142° C.

I claim:

1. A process for the preparation of a compound of the formula

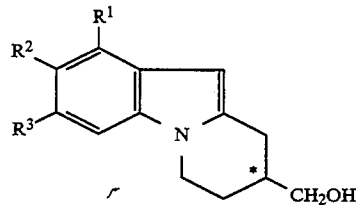

I wherein R$^1$, R$^2$ and R$^3$ each, independently, is hydrogen, halogen, C$_{1-7}$-alkyl, C$_{1-7}$-haloalkyl, hydroxy, C$_{1-7}$-alkoxy, C$_{1-7}$-alkylthio, C$_{1-7}$-alkylsulfinyl, C$_{1-7}$-alkylsulfonyl, nitro, amino or acylamino and the asterisk (*) denotes the chiral center, in the (S)- or (R)-form, which process comprises asymmetrically hydrogenation the corresponding 6,7-dihydropyrido[1,2-a]indole-8-methanol of the formula $$\begin{array}{c} R^1 \\ R^2 \\ R^3 \end{array} \diagram{indole-tetrahydropyridine with CH_2OH} \quad \text{II}$$

wherein $R^1$, $R^2$ and $R^3$ have the significances given above, in the presence of an optically active rhodium-diphosphine complex.

2. A process according to claim 1, wherein the optically active rhodium-diphosphine complex is a complex of the formula $$[Rh(X)(Y)(L)_m]_n \qquad \text{III}$$

or $$[Rh(Y)(L)_m]^+ A^- \qquad \text{IV}$$

wherein

X is a coordinating anionic ligand,
Y is an optically active atropisomeric diphosphine ligand,
L is a neutral ligand,
m is 0, 1 or 2,
n is 1 or 2 and
$A^-$ is a non-coordinating anion.

3. A process according to claim 2, wherein the optically active rhodium-diphosphine complex is a complex of the general formula $$[Rh(X^1)(Y^1)(L^1)_m]_n \qquad \text{III}'$$

or $$[Rh(Y^1)(L^1)_m9^+(A^1)^- \qquad \text{IV}'$$

wherein $X^1$ is a halide, an anion $R^4$—COO—, an anion $R^4$—SO$_3^-$, 1,3-diketone or phenolate optionally mono- or multiply-substituted with lower alkyl and/or halogen,
$Y^1$ is an optically active atropisomeric diphosphine ligand of the formula $$\diagram{biphenyl with (R^9)_p, R^5, R^6, P(R^7)_2, P(R^8)_2} \qquad \text{V}$$

or of the formula $$\diagram{binaphthyl with (R^{12})_p, P(R^7)_2, P(R^8)_2} \qquad \text{VI}$$

$L^1$, or each $L^1$, independently, is an olefinic ligand, a nitrile or a solvent molecule,
$(A^1)^-$ is $BH_4^-$, $ClO_4^-$ or $PF_6^-$,
m is 0, 1 or 2,
n is 1 or 2,
$R^4$ is lower alkyl, halogenated lower alkyl or aryl,
$R^5$ and $R^6$ each, independently, is lower alkyl, lower alkoxy, di(lower alkyl)amino, hydroxy, protected hydroxy, hydroxymethyl or protected hydroxymethyl
$R^5$ and $R^6$, taken together, are a divalent group of the formula $$-(CH_2)_q-, \quad -CH_2-O-CH_2-,$$

$$\begin{array}{c}-CH_2\\ \phantom{x} \\ -CH_2\end{array}\!\!\!\!N-R^{10} \text{ or } \begin{array}{c}-CH_2\\ \phantom{x} \\ -CH_2\end{array}\!\!\!\!C\begin{array}{c}OR^{11}\\ \phantom{x} \\ OR^{11}\end{array}$$

$R^7$ and $R^8$ each, independently, is lower alkyl, $C_{3-7}$-cycloalkyl, optionally substituted phenyl, a five-membered heteroaromatic or a group of the formula $$\diagram{dibenzophosphole}$$

$R^9$ is lower alkyl or lower alkoxy,
$R^{10}$ is lower alkyl, optionally substituted phenyl or optionally substituted benzyl,
$R^{11}$ is lower alkyl or both $R^{11}$'s, taken together are di- or trimethylene,
$R^{12}$ is halogen, hydroxy, methyl, ethyl, amino, acetamido, nitro or sulfo,
p is zero or the number 1, 2 or 3
and q is the number 3, 4 or 5.

4. A process according to claim 3, wherein (S)-6,7,8,9-tetrahydropyrido[1,2-a]indole-8-methanol is prepared starting with 6,7-dihydropyrido[1,2-a]indole-8-methanol.

5. A process according to claim 4, wherein a complex of formula III or III' is the optically active rhodium-diphosphine complex.

6. A compound of the formula $$\begin{array}{c} R^1 \\ R^2 \\ R^3 \end{array} \diagram{indole-tetrahydropyridine with CH_2OH} \qquad \text{II}$$

wherein $R^1$, $R^2$ and $R^3$ each, independently, is hydrogen, halogen, $C_{1-7}$-alkylthio, $C_{1-7}$-alkylsulfinyl, $C_{1-7}$-alkylsulfonyl, nitro, amino or acylamino.

* * * * *